(12) United States Patent
Ogawa et al.

(10) Patent No.: US 7,145,146 B2
(45) Date of Patent: Dec. 5, 2006

(54) MICRO-SPECTROSCOPIC MEASURING DEVICE AND MICRO-CHEMICAL SYSTEM

(75) Inventors: Taro Ogawa, Tokyo (JP); Toshiki Sugawara, Kodaira (JP); Kazuhiko Hosomi, Tachikawa (JP); Masataka Shirai, Higashimurayama (JP); Toshio Katsuyama, Ome (JP); Kaoru Umemura, Tokyo (JP); Masaru Izawa, Hino (JP); Kazuhiko Sagara, Kodaira (JP); Hiroshi Kakibayashi, Nagareyama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/788,275

(22) Filed: Mar. 1, 2004

(65) Prior Publication Data

US 2005/0017178 A1    Jan. 27, 2005

(30) Foreign Application Priority Data

Jul. 23, 2003    (JP) .............................. 2003-200191

(51) Int. Cl.
    *G01N 21/35*    (2006.01)
(52) U.S. Cl. ................................. 250/339.07
(58) Field of Classification Search ............ 250/339.07
    See application file for complete search history.

(56) References Cited

U.S. PATENT DOCUMENTS 5,446,534 A    8/1995    Goldman

2001/0028932 A1    10/2001   Church et al.
2003/0017079 A1    1/2003    Hahn et al.
2004/0008437 A1*   1/2004    Kittaka et al. .............. 359/883

FOREIGN PATENT DOCUMENTS

EP    1136853    9/2001
GB    2383127    6/2003

OTHER PUBLICATIONS

"Material Analysis by Infrared Method", K. Nishikida et al, Kodansha.
Technical Information Association Seminar Text, "Photonic Crystal Manufacture", Micromachining Technology and Optical Properties Control.
"Thin Sold Films 300", 1997, Elsevier, pp. 289-294.
Krauss, Thomas F., "Planar Photonic Crystal Waveguide Devices for Integrated Optics", Phys. Stat. Sol. vol., 197, No. 3, Jun. 20, 2003, pp. 688-702.
Adams, Mark L. et al, "Microfluidic Integration on Detector Arrays for Absorption and Fluorescence Micro-Spectrometers", Elsevier Science B.V., vol. 104, No. 1, Mar. 15, 2003, pp. 25-31.

* cited by examiner

*Primary Examiner*—Albert J. Gagliardi
*Assistant Examiner*—Marcus Taningco
(74) *Attorney, Agent, or Firm*—Mattingly, Stanger, Malur & Brundidge, P.C.

(57) ABSTRACT

A micro-spectroscopic measuring device having a structure in which a spectroscopic element made of an array of photonic crystals with defects, flow paths for introducing a sample, and light detecting elements with sensitivity to a band from near infrared to infrared are stacked.

16 Claims, 11 Drawing Sheets

FIG. 5
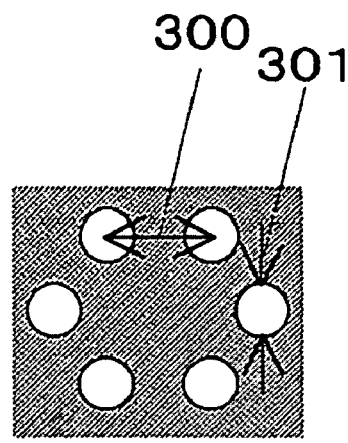
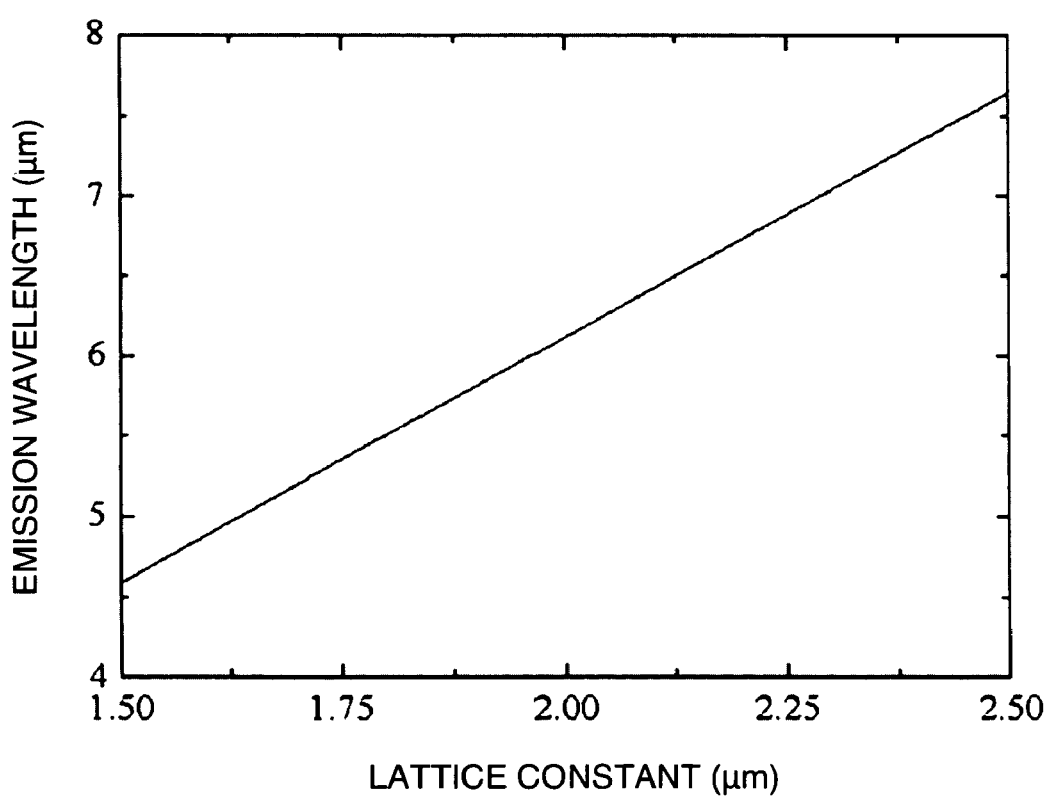

MICRO-SPECTROSCOPIC MEASURING DEVICE AND MICRO-CHEMICAL SYSTEM

BACKGROUND OF THE INVENTION

The present invention relates to a micro-chemical system for on-chip implementation of chemical-synthetic and chemical-analytic operations by employing micro-electro-mechanical systems (MEMS) technology, and also relates to a micro-spectroscopic measuring device necessary for the micro-chemical system, manufacturing methods therefore and application methods thereof.

As the basic infrastructure supporting the chemical industries of today, there are the chemical plants that supply various synthetic materials. In the sector of chemical plants, the technology currently drawing attention from the viewpoint of comprehensive cost reduction, such as energy savings and environmental impact alleviations by decreasing reaction byproducts and cutting down the plant floor spaces, etc. is the micro-chemical system, which integrates chemical reaction operations on an on-chip plant by employing MEMS technology. FIGS. 1 and 2 are a conceptual diagram of a micro-chemical plant and a conceptual diagram of micro-chemical unit operations.

In FIG. 1, reference numeral 1 denotes a substrate of glass or silicon (Si), for example; 2 denotes a sample flow path several tens of μm to 100 μm in width and depth formed in the substrate; 3, 4, 5, 6, 7 and 8 denote drains; 9, 310, 11 and 12 denote micro pumps; 13 denotes a micro valve; 14 denotes a temperature control mechanism; 15, 16 and 17 denote connectors; 18, 19 and 20 denote connecting operation of connectors; 21 and 22 denote injection of material; 23 denotes extraction of synthesized substance; and 24 denotes a complete system of a micro-chemical plant.

To begin with, the connectors 15, 16 are connected to the drains 3, 4, and materials 21, 22 are supplied. Then, the valve 13 is opened, the sample materials are fed by the pumps 9, 10, and the valve 13 is opened to feed the materials to the flow path 2. Next, the temperature controller 14 is actuated for heating or cooling. As a result, as shown in FIG. 2, chemical unit operations take place, such as mixing•reaction, phase separation•phase conjunction, heating, and molecule manipulation•solvent extraction. Furthermore, the connector 17 is connected to the drain 7, making it possible to extract a synthetic substance 23.

In the micro-chemical system, as shown in FIG. 2, as the micro fluid size becomes smaller, the unit chemical reactions, such as mixing•reaction, phase separation•phase conjunction, heat generation, and molecule transport•solvent extraction, take place with high efficiency in proportion to the square or the cube of the size of the fluid. Therefore, the micro-chemical system is not only suitable for large-item small-volume production of chemical synthetic substances but also because it increases the yield per unit volume of material, it realizes high-efficiency mass production. Moreover, it becomes possible to decrease the quantity of reaction byproducts generated during synthesis.

To the manufacture of components of the micro-chemical system, such as the micro flow paths, micro valves, and the micro temperature controller, the existing ultra-micro machining technology in MEMS and semiconductor fabrication can be applied. In addition to chemical synthesis, expectations are held high for the micro-chemical system to be applied to analysis of environmental pollutants, such as endocrine disrupters, and dioxins or to analysis of biological substances, such as blood and DNA.

In chemical plants such as this, some means such as identification or quantitative analysis of reaction products means is generally required to measure in real time various properties of products. In the con-ventional micro-chemical systems, no such appropriate means are available.

SUMMARY OF THE INVENTION

In micro-chemical plants in the past, as mentioned above, there was no adequate means for measuring the properties of reaction products in real time. Above all else, there was not means for spectroscopic measurement.

The object of the present invention is to provide means capable of spectroscopic measurement of the properties of minute quantities of chemical substances and particularly to provide means for spectroscopic measurement of properties suitable for micro-chemical plants.

In the present invention, the above-mentioned "means for spectroscopic measurement of minute quantities of chemical substances" is referred to as a micro-spectroscopic measuring device.

In a micro-spectroscopic measuring device according to the present invention, the micro-spectroscopic measuring device is realized by mounting micro-spectroscopic elements, sample flow paths, and light detecting elements in high integration on a chip several square centimeters or less. Those elements are integrated on the same substrate by semiconductor process technology.

When used for the micro-spectroscopic element, a photonic crystal is advantageous in miniaturizing the size of the element.

The above-mentioned micro-spectroscopic measuring device is capable of measuring the spectrum of light of any wavelength by virtue of the characteristics of the light source and the spectroscopic element. When the micro-chemical plant is applied to pharmaceutical plants or organic chemical plants, an element with sensitivity to a range of from near infrared to infrared wavelengths is suitable for the light detecting elements. This is because substances handled in those sectors are most likely to be biological or organic materials.

Other objects, features and advantages of the invention will become apparent from the following description of the embodiments of the invention taken in conjunction with the accompanying drawings.

BRIEF DESCRIPTION OF THE DRAWINGS

FIG. 5 shows the correlation between the lattice constant and the emission wavelength of a photonic crystal in which donor type defects were introduced and which is used as a spectroscopic element of the micro-spectroscopic measuring device according to the present invention;

DESCRIPTION OF THE EMBODIMENTS

Some embodiments of the present invention will be described with reference to the accompanying drawings. Needless to say, the technical scope of the present invention is not limited to the structures of those embodiments.

First Embodiment

Figure 1:
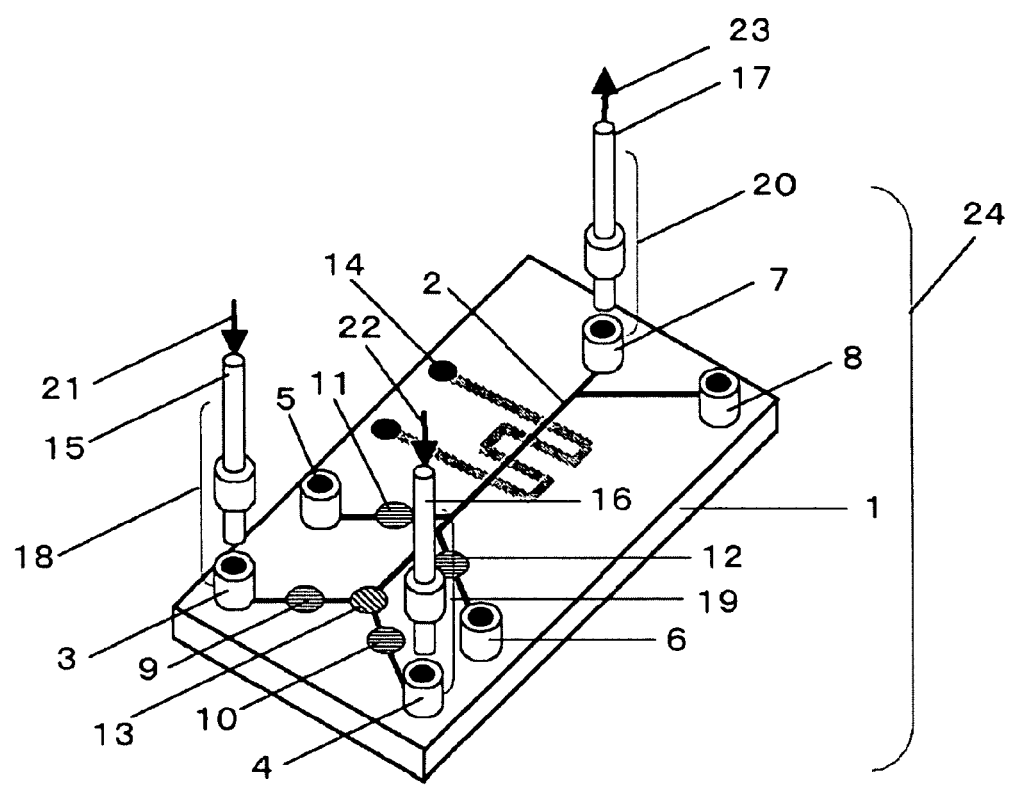
FIG. 1 is a conceptual diagram of a micro-chemical plant.
Figure 2:
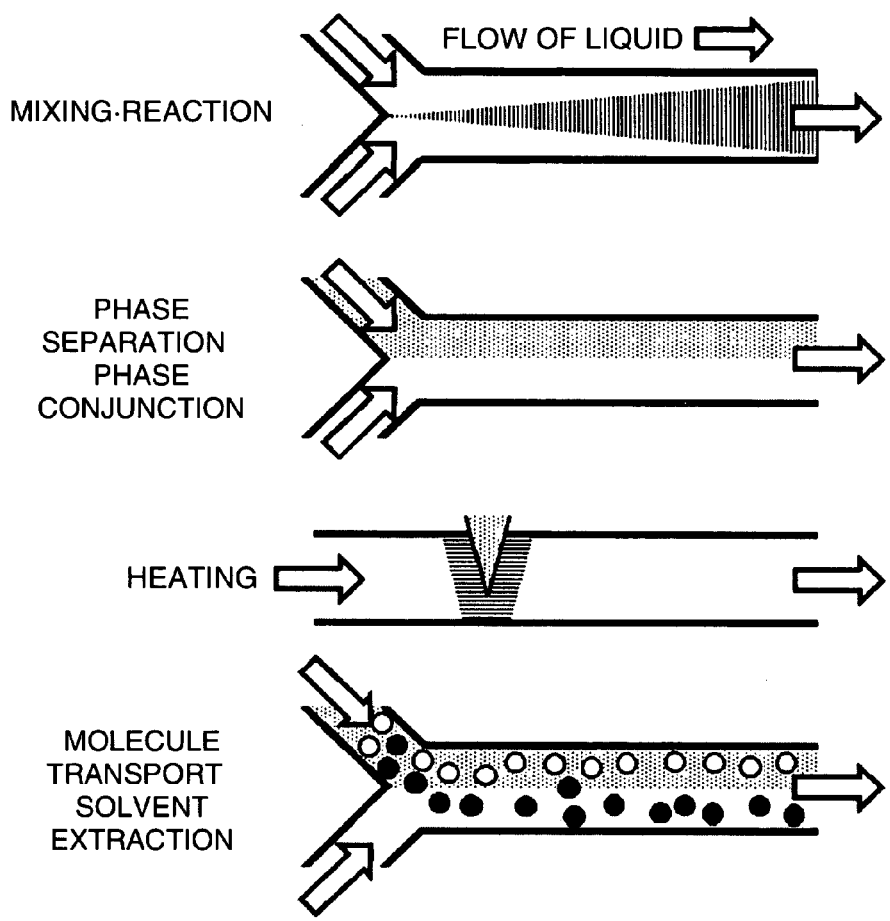
FIG. 2 is a conceptual diagram of micro-chemical unit operations.
Figure 3:
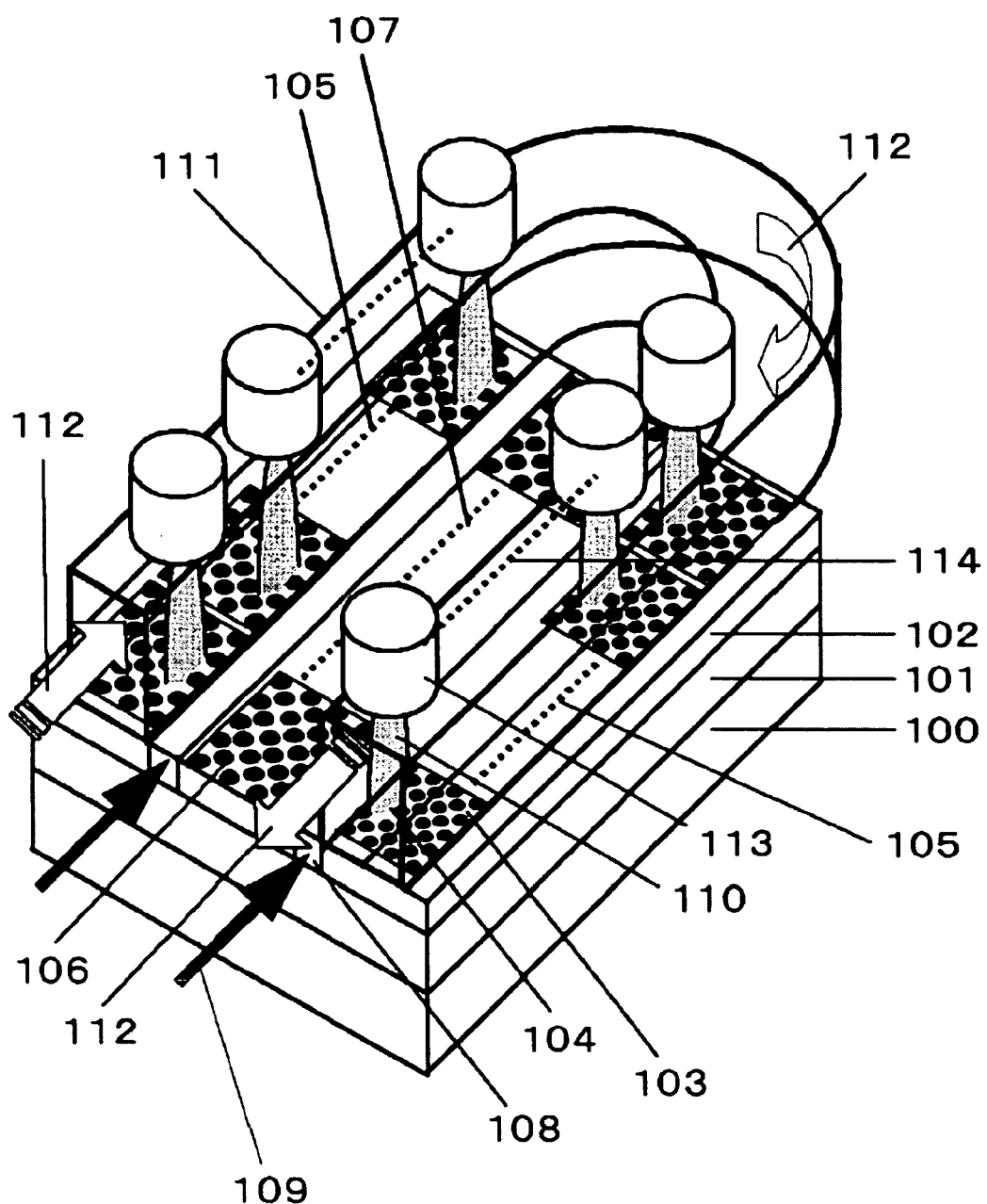
FIG. 3 is a conceptual diagram of a micro-spectroscopic measuring device according to the present invention.

FIG. 3 is a conceptual diagram showing an example of a micro-spectroscopic measuring device according to the first embodiment. Reference numeral 100 denotes a Si substrate; 101 denotes a Si-oxide clad layer with a thickness of about 3 μm; 102 denotes a photonic crystal layer of Si with a thickness of about 1 μm; 103 denotes a basic unit of the defect-containing photonic crystal 102 having cylindrical holes formed in a triangular lattice structure; 104 denotes a donor-type defect provided in each basic unit 103 of the defect-containing photonic crystal, in which the patterned holes are embedded at lattice points at a single of or a plurality of the above-mentioned triangular lattice; 105 denotes an array of a plurality of basic units 103 of the defect-containing photonic crystal, in which the lattice constant of the triangular lattice or the hole diameter of the patterned holes varies from one hole to another; 106 denotes a basis unit of a defect-free photonic crystal; 107 denotes an array of a plurality of basic units 106 of the defect-free photonic crystal; 108 denotes a light waveguide provided in the photonic crystal layer 102; 109 denotes a white infrared light introduced in the light waveguide 108; 110 denotes an emitted infrared light beam emitted from a defect portion 104 of the basic unit 103 of the defect-containing photonic crystal; 111 denotes a sample micro flow path about several tens of μm to 100 μm in width and depth formed in a material, such as Si almost transparent to infrared light; 112 denotes the flow of liquid sample fed into the sample micro flow path 111; 113 denotes light detecting elements having linear response to infrared wavelengths such as a pyroelectric capacitor, or a lead sulfide (PbS) or lead selenide (PbSe) photoconductor, for example, mounted above a defect 104 in the basic unit 103 of the defect-containing photonic crystal through the intermediary of the sample micro flow path 111; and 114 denotes an array of the light detecting elements 113 disposed above the array 105 of the basic units 103 of the defect-containing photonic crystal.

In this first embodiment, the photonic crystal is defined as an "optical material with a microstructure of periodic refractive index distribution". The refractive index distribution is sometimes provided in one-dimensional or two-dimensional or three-dimensional directions.

When an infrared light 109 is introduced into the light waveguide 108 close to the photonic crystal having formed thereon the triangular lattice points formed as the circular holes open to the Si substrate 100, the Si oxide film layer 101 and the clad layer 102, an infrared light 110 split into an almost monochromatic light is emitted from the defects 104 of the photonic crystal 103. The principle of this phenomenon will be described in the following. The photonic crystal has a specific periodic structure organized in the crystal, and its period is about the wavelength of light used. In a two-dimensional photonic crystal, by its periodic structure, a light forbidden band is formed in the so-called photonic band structure, so that light of a specific wavelength cannot exist in the crystal. In this respect, when defects are set up in the periodic structure of the photonic crystal to use them as light-emitters and a white light is introduced from the light introducing part, a specific light ray which should be impossible to exist in the crystal emits from the defects. Therefore, by providing a flow path 111 made of a material transparent to infrared light right on the defect portions 104 of the photonic crystal and supplying the liquid sample 112 into the flow path and mounting light detecting elements 113 on the flow path 111, the emitted infrared light 110 that comes passing or scattering through the sample 112 that flows through the flow path can be detected by the light detecting elements 113, so that the light absorbency to an emitted infrared light 110 of a specific wavelength can be measured. Furthermore, the wavelength of the emitted infrared light can be varied either to a short wavelength or a long wavelength by changing the lattice constant or the hole diameter of the photonic crystal. Therefore, by arranging a plurality of the basic units 103 of a defect-containing photonic crystal, which have different lattice constants or different hole diameters, in an array configuration 105, it becomes possible to measure the light absorbency, in other words, the absorption spectrum of each of different wavelengths can be measured. Since the basic units 103 of the defect-containing photonic crystal are about several tens of μm, even if 100 pieces of basic units 103 of a defect-containing photonic crystal are arranged and an array 105 of 100 channels is provided, for example, they can be integrated on a several-cm-square chip. In this case, inside the array 105, it is desirable to arrange the basic units 103 of the defect-containing photonic crystal in order of the lattice constant or the hole diameter of the photonic crystal. If done in this manner, a spectroscopy spectrum can be obtained by collecting data on absorbency corresponding to the basic units 103 in the order in which they are arranged.

Though in FIG. 3 the sample flow path 111 is laid in the U-form, the flow path may be in a straight, folded U-form, S-form, or any other form as necessity requires. Moreover, the basic units 103 of the defect-containing photonic crystal can be arranged along the shape of the flow path. Further, in addition to the basic units 103 of the defect-containing photonic crystal being arranged along the basic units 103 of the defect-containing photonic crystal, the flow path may be formed in a structure that fills the gap between the array 105 of the photonic crystal serving as the spectroscopic element 200 and the light detecting elements 113.

The photonic crystal in the present embodiment is a so-called two-dimensional photonic crystal. In conjunction with the two-dimensional photonic crystal, in the Si layer of a Silicon on Insulator (SOI) substrate, cylindrical through-holes are formed by optical or X-ray or electron-beam lithography and/or dry etching by plasma or the like. Those through-holes are arranged in a triangular lattice structure as viewed from the surface of the Si layer. The through-holes may be filled with a material such as barium titanate. The material of the layer, in which the through-holes are formed, need not necessarily be Si but may be a second material other than the material in which the through-holes are formed. The second material may be air or vacuum, in other words, the two-dimensional photonic crystal can be formed as long as the materials formed in a columnar structure are disposed in a triangular lattice structure. The lattice points in the photonic crystals 103, 106 are not limited to those arranged in a triangular lattice structure, but may be arranged in a square lattice or in any other array so long as a forbidden band is formed to light rays of certain wavelengths in the optical energy band. The light waveguide 108 is not limited to line defect waveguides, but may be a waveguide in any form of defect as long as it acts as a light waveguide.

The photonic crystal 103 or 106 may be formed as a one-dimensional photonic crystal by providing a plate-shaped through-hole in the Si layer, or providing a plate-shaped Si layer in the vacuum or air or in a layer of any other material, or by creating a so-called one-dimensional photonic crystal made up of a plate-shaped through-hole and a plate-shaped Si layer disposed in parallel. The Si layer may be replaced by some other material, such as barium titanate.

The defect provided in the basic unit 103 of the defect-containing photonic crystal may be formed by filling up a single or multiple lattice points or by using not only a donor-type defect in which the diameter of the lattice points is reduced but also an acceptor-type defect in which the diameter of a single or multiple lattice points is enlarged.

A desirable photonic crystal may be obtained from a so-called three-dimensional photonic crystal in which a material with a high refractive index and a material with a low refractive index to light rays of near infrared to infrared wavelengths are arranged in a diamond crystal structure.

TABLE 1

| Material | Refractive index (n) | Source |
| --- | --- | --- |
| Air | 1 | Literature 2 |
| SiO$_2$ (Glass) | 1.46 | Literature 2 |
| Fused silica | 1.43 | Literature 1 |
| Crystal | 1.5 | Literature 1 |
| NaCl | 1.54 | Literature 1 |
| Al$_2$O$_3$ | 1.7 | Literature 2 |
| KBr | 1.52 | Literature 1 |
| CsBr | 1.66 | Literature 1 |
| CsI | 1.74 | Literature 1 |
| CaF2 | 1.39 | Literature 1 |
| BaF2 | 1.42 | Literature 1 |
| AgBr | ~2.2 | Literature 1 |
| ZnS | 2.2 | Literature 1 |
| ZnSe | 2.41 | Literature 1 |
| MgO | 1.74 | Literature 2 |
| Polymer | 1.4–1.6 | Literature 2 |
| GeO$_2$ | 2 | Literature 2 |
| TiO$_2$ | 2.72 | Literature 2 |
| InP | 3.1 | Literature 2 |
| GaAs | 3.6 | Literature 2 |
| Si | 3.5 | Literature 2 |
| Ge | 4.1 | Literature 2 |
| Te | 4.3($\parallel$) 6.3($\perp$) | Literature 1 |
| BaTiO$_3$ | ~2.0 | Literature 3 |

Table 1 shows refractive indices of various materials for infrared wavelengths described in literature 1, "Material Analysis by Infrared Method" by Koichi Nishikida, Reikichi Iwamoto, Kodansha; literature 2, Technical Information Association Seminar Text, "Photonic Crystal Manufacture, Micromachining Technology and Optical Properties Control; and literature 3, "Thin Solid Films 300" (1997), pp. 289–294, ELSEVIER. According to Table 1, a photonic crystal is preferably formed by combining materials in such a way that the ratio of refractive indices of high and low refraction materials is 2 or greater, but other materials may be used.

The Si layer 102 where the photonic crystals 103 and 106 are formed, the flow path 111, and the light detecting element 113 are preferably positioned in contact with each other to reduce loss of light; however, if the light which is emitted from photonic crystals 103, 106 and passed through or dispersed by the sample flowing through the flow path 111 can be detected by the light detecting elements 113, they need not be positioned in contact with each other and a proper gap may be provided by using spacers, for example.

When spectroscopic measurement is performed by using a micro-spectroscopic measuring device according to the present invention, it is advisable to previously feed an amount of sample for reference for spectrum measured from a sample before measurement and obtain a reference spectrum to be used as reference. Moreover, it is possible to provide a plurality of flow paths or micro-spectroscopic measuring devices, supply a reference sample on one side and supply a sample to be measured on another side, and compare measured spectra with the reference spectrum.

As has been described above, by forming or stacking a spectroscopic element and light detecting elements and sample-flow paths formed between those elements on a single substrate, it is possible to provide a so-called micro-spectroscopic measuring device which has integrated on a chip not more than several centimeters square such functions as to identify molecules by measuring a absorption spectrum of reaction products or to measure their quantities produced. It is also possible to connect or integrate the micro-spectroscopic measuring device to a micro-chemical plant, in other words, spectroscopic measurement becomes possible also on a micro-chemical system which uses the micro-chemical plant.

Second Embodiment

Figure 4:
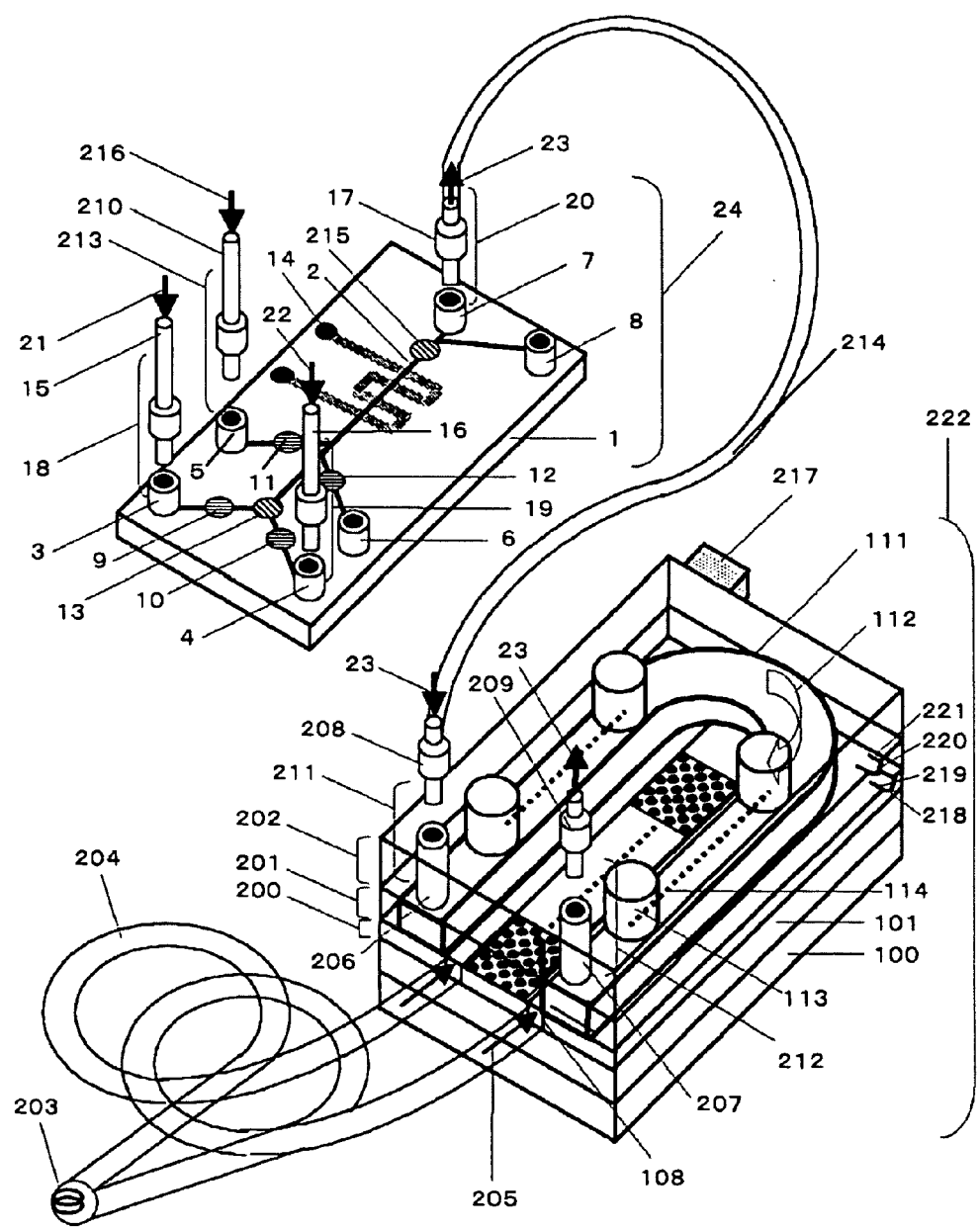
FIG. 4 is a micro-chemical system formed by attaching a micro-spectroscopic measuring device according to the present invention to a micro-chemical plant.

Another embodiment of the present invention will be described with reference to FIG. 4. FIG. 4 shows an example of a micro-chemical system in which the micro-spectroscopic measuring device is connected to the micro-chemical plant. In FIG. 4, 200 denotes a spectroscopic element made up of an array of a repetitive pattern of basic units of the defect-containing photonic crystal on the Si layer, wherein the basic units are arranged such that the lattice constant of the lattice points of the adjacent basic units gradually increases or decreases; 201 denotes a Si layer in which the flow path 111 of 50 μm width and 50 μm depth is formed; 202 denotes a light-detecting-element mounted layer including an array 114 of the light detecting elements 113 and circuits necessary to supply power for light-detecting operation and to measure the intensity of signals from the light detecting elements; 203 denotes an infrared light source; 204 denotes a polarization optical fiber; 205 denotes an infrared light polarized in TE mode; 206, 207 denote drains; 208, 209, 210 denote nozzles; 211, 212, 213 connection of nozzles to drains; 214 denotes a capillary tube to guide sample; 215 denotes a micro pump; 216 denotes material; 217 denotes a connector attached to the light-detecting-element mounted layer 202; 218 denotes V-grooves provided at the four corners of the spectroscopic element 200; 219 denotes V-projections provided at the four corners of the Si layer 201; 220 denotes V-grooves provided at the four corners of the Si layer 201; 221 denotes V-projections provided at the light-detector mounted layer 202; and 222 denotes a complete system of the micro-spectroscopic measuring device.

First, the nozzles 15, 16, 210 were connected to the drains 3, 4, 5 of the micro-chemical plant 24. Then, materials 21, 22, 216 were supplied to the nozzles 15, 16, 210. The materials were fed through the flow path 2 of 100 µm width by the micro pumps 9, 10, 11 for mixing, reaction and phase separation. As a result of a mixture being heated by the temperature controller 14, a synthetic material 23 was produced. As the synthetic material 23 was pressurized by the micro pump 215, and guided by the tube 214 through the nozzle 208 and the drain 211 to the flow path 111 in the micro-spectroscopic measuring device 217. In this embodiment, ethyl acetate was synthesized as an example of a synthesized material 23.

Figure 6:
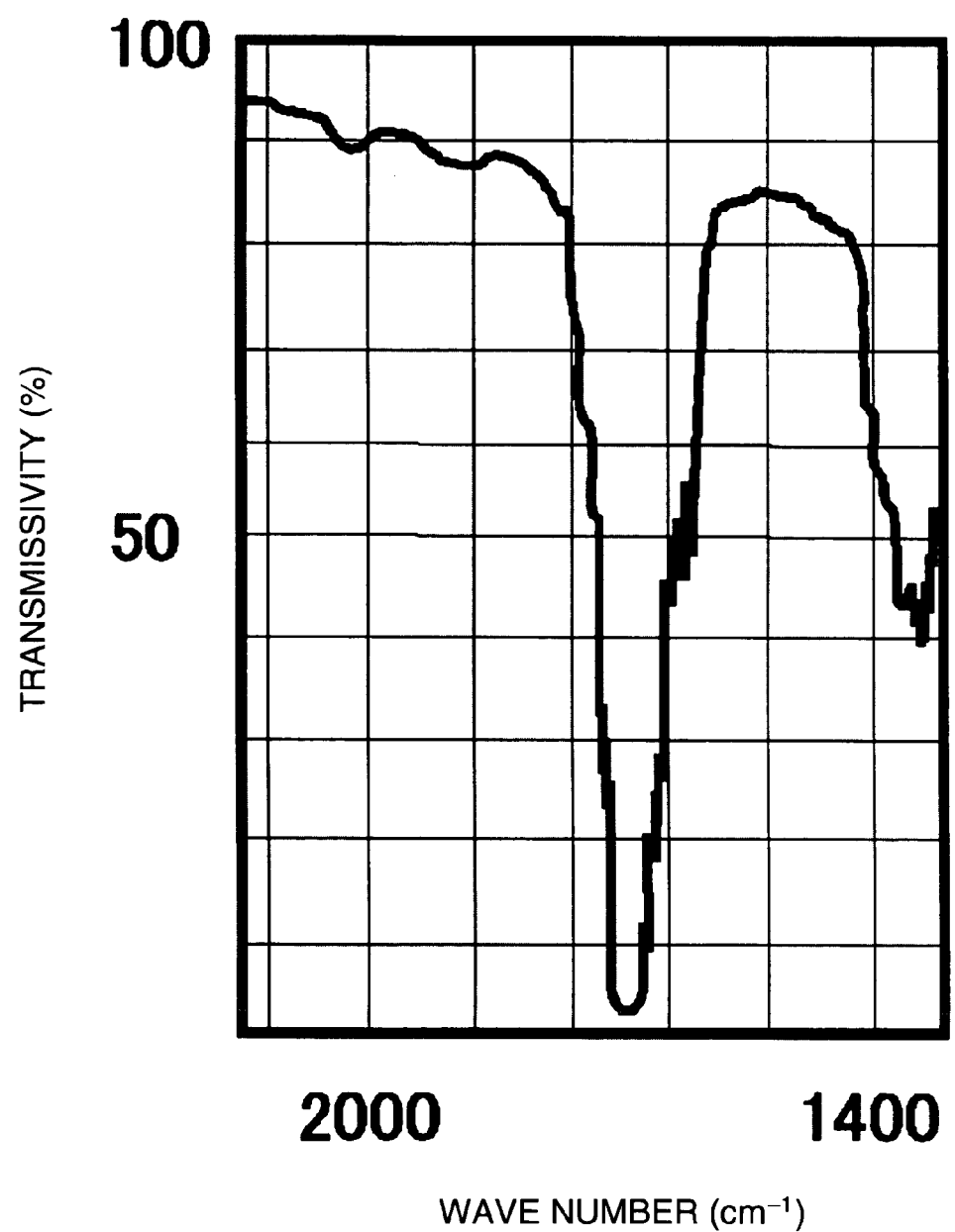
FIG. 6 shows a measurement result of infrared absorption spectrum of ethyl acetate measured by the micro-spectroscopic measuring device according to the present invention.

FIG. 5 shows an example of a photonic crystal which has a donor defect introduced by removing one hole, and which is used in the spectroscopic element of the micro-spectroscopic measuring device. In FIG. 5, 300 denotes the lattice constant of the photonic crystal and 301 denotes the diameter of a hole of the photonic crystal. FIG. 5 also shows the lattice constant dependency of emission wavelengths when the lattice constant 300 was varied to a diameter of a hole of 700 nm. As shown in FIG. 5, the spectral wavelength could be shifted toward the long wavelength about 3000 nm by increasing the lattice constant of the photonic crystal by 1000 nm. Therefore, by arranging the defect-containing basic units in two arrays, each array comprising 50 basic units in which the lattice constant is shifted by 8 nm each for every basic unit between 1600 nm and 2450 nm, it is possible, at the light-detecting-element circuit layer 202 via the flow path 111, to measure emitted infrared light having a wavelength shift of 25 nm and a wave-number shift of 4 $cm^{-1}$ in a wavelength range of 5000 nm to 7500 nm and a wave number range of 2000 $cm^{-1}$ to 1350 $cm^{-1}$. As a result of external processing of measured signals through the connector 217, as shown in FIG. 6, in a range of 2000 $cm^{-1}$ to 1350 $cm^{-1}$, a sharp absorption resulting from C=O stretching was observed in the neighborhood of 1745 $cm^{-1}$ and synthesis of ethyl acetate was confirmed.

Though the emission wavelength is varied by varying the lattice constant of the basic units of the adjacent defect-containing photonic crystals in this embodiment, the emission wavelength can be varied by varying the hole diameter of the basic units of the adjacent defect-containing photonic crystals or by varying both of the lattice constant and the hole diameter. When the photonic crystals are formed by using semiconductor fabrication technology, fabrication can be made easier if the lattice constant is varied. If the hole diameter is varied, there is a possibility that the intensity of wavelength components other than a desired wavelength increases. However, if there is wavelength dispersion in the refraction index of a photonic crystal, it is possible to correct the emission wavelength according to the wavelength dispersion by varying the hole diameter as well as the lattice constant.

As to the lattice constant of the basic unit of the photonic crystal including defects, hole diameter, and further hole diameter and the lattice constant, it is preferable that a plurality of basic units having such items slightly changed are arranged in the order of magnitude of the hole diameter or lattice constant; however, such order may be arranged in a random order.

In this embodiment, it is designed that the spectral wavelengths of the micro-spectroscope are 5000 nm to 7500 nm, that is, an infrared wavelength bandwidth, but the wavelengths used are not limited to the infrared wavelength bandwidth. For example, by changing the size of the spectroscopic element 200 formed of an array of photonic crystals but maintaining the similar figure, and by changing the material for the photonic crystal, the so-called photonic band is changed, and therefore the spectral wavelength bandwidth can be changed to a desired bandwidth. By changing the material of the sample flow path and the kind of the light detecting element attending on a change in the spectral wavelength bandwidth, it becomes possible to use the micro-spectroscopic measuring device according to the present invention in a bandwidth of near infrared, visible radiation and ultra-violet radiation.

In this embodiment, there are provided the V-grooves 218 at the four corners of the spectroscopic element 200, the V-projections 219 at the four corners of the Si layer 201, the V-grooves 220, and the V-projections 221 on the light-detecting-element mounted layer 202. Those grooves are provided for use as alignment devices or marks when various structural blocks are positioned; therefore, when the flow paths have become deteriorated and need to be replaced, positioning and reassembling of them can be made easily. Note that the alignment devices or marks are not limited to V-shaped grooves and, needless to say, they may be in some other structure or shape.

In this embodiment, the infrared light source 203 and the optical fiber 204 are provided separate from the substrate 100, but those parts or other parts such as a polarization element may be mounted on the substrate 100.

If a pyroelectric capacitor of barium titanate, lead germanate or glycine sulfate (TGS) is used for the light detecting element 113, a high detection sensitivity can be obtained by intermittently blocking the infrared light 205 with a chopper.

In addition to a liquid sample, a liquid with dissolved particulates or a gas may be used for spectroscopic measurement. Moreover, in stead of the Si layer 201 having the flow paths 111 formed therein, by mounting a thin-film sample between the spectroscopic element 200 and the light-detecting-element mounted layer 202, solid samples can be measured.

A power source such as a battery or a generator unit, a memory and a communication function may be added to the micro-spectroscopic measuring device unit. By installing a single unit or a plurality of such units at a plurality of fixed points in the environment, it becomes possible to measure infrared absorption data on endocrine disrupters or dioxins in lakes, oceans or in soil, so that it becomes possible to identify and quantify environmental pollutants and to obtain distribution data of those substances.

Similarly, by mounting the micro-spectroscopic measuring device equipped with a power source such as battery or a generator, a memory and a communication device to health care equipment, it becomes possible to measure infrared absorption data on chemical substances, such as the blood plasma density, protein, sugar content in blood or urine, for example, so that it becomes possible to identify and quantify those substances.

Third Embodiment

Figure 7:
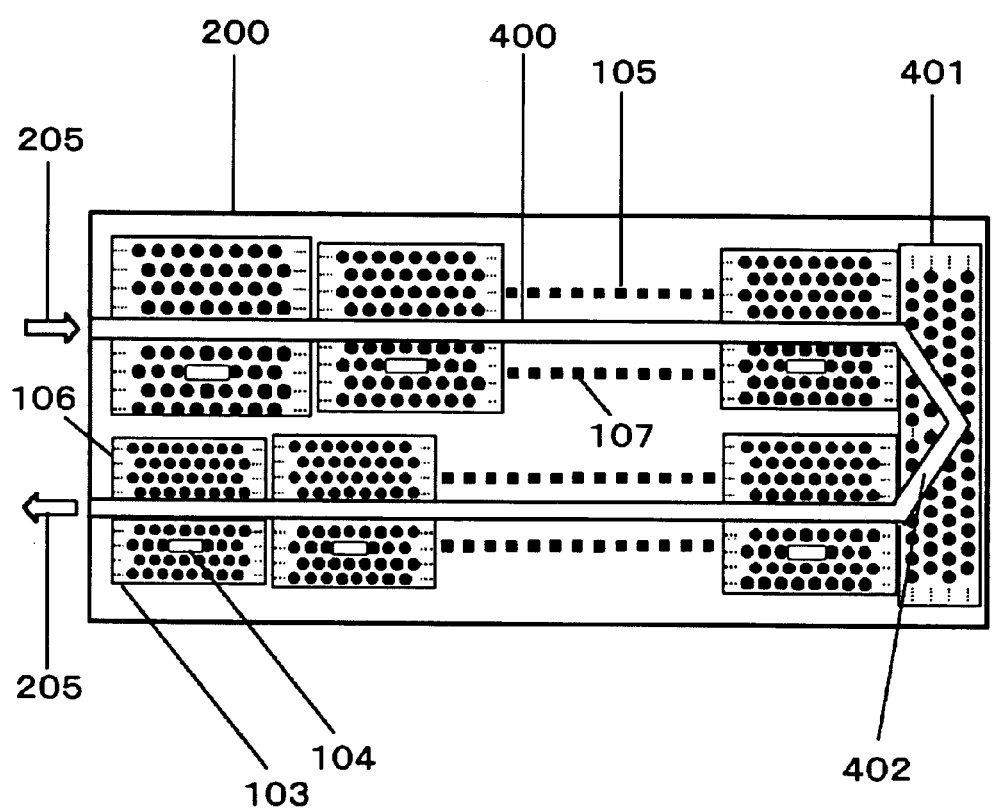
FIG. 7 is a plan view of the spectroscopic element formed by an array of photonic crystals used in the micro-spectroscopic measuring device according to the present invention.

In this embodiment, description will be made of a case where changes are carried out in the photonic crystal and the method of applying infrared light used in the micro-spectroscopic measuring device. FIG. 7 is a plan view of the spectroscopic element 200 formed of an array of photonic crystals, in which 400 denotes a straight waveguide for infrared light. The straight waveguide 400 may be a line-defect waveguide, but it is not limited to the line-detect waveguide. It is satisfied if it has a function operable as a path to guide light. Reference numeral 401 denotes a photonic crystal, and 402 denotes a line-defect waveguide in the photonic crystal.

In this embodiment, as shown in FIG. 7, a loop-back portion of the straight waveguide 402 is provided in the photonic crystal 401, thus enabling infrared light propagation without loss due to the loop-back of light. Therefore, in contrast to the first embodiment, it is possible to configure the spectroscopic element with infrared light injected only in one direction.

Fourth Embodiment

Figure 8:
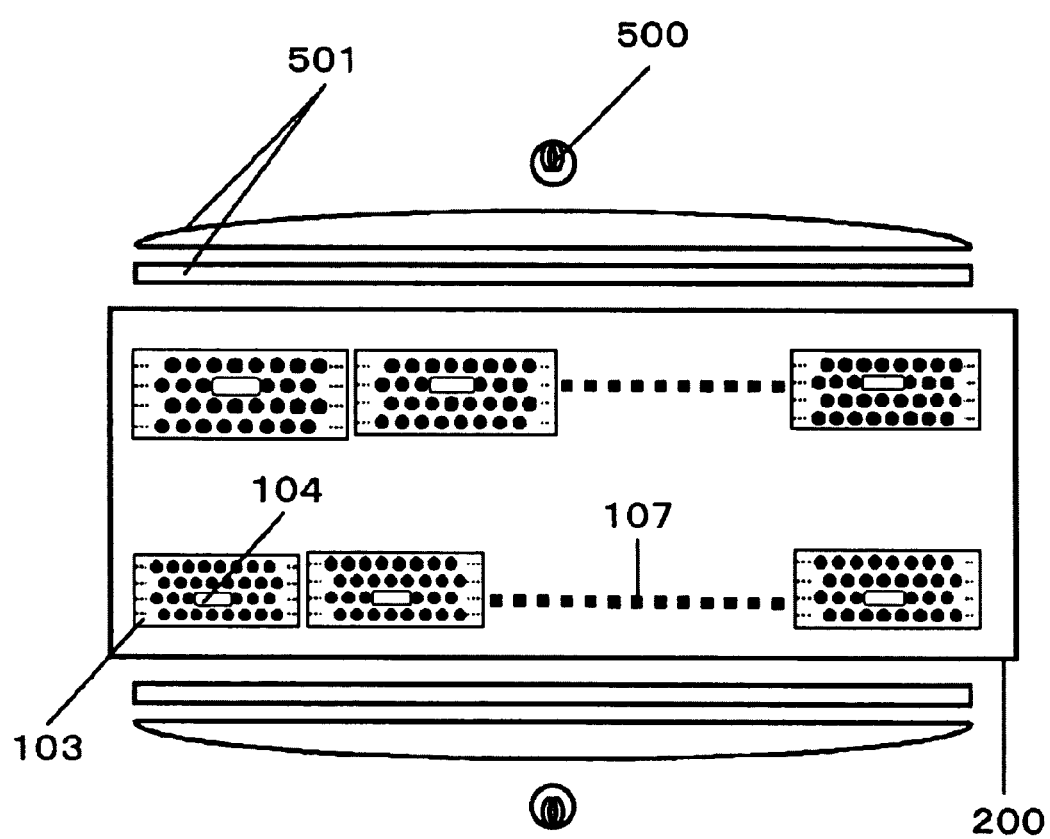
FIG. 8 is a plan view of the spectroscopic element formed by an array of photonic crystals used in the micro-spectroscopic measuring device according to the present invention.

In this embodiment, description will be made of a case where changes are carried out in the photonic crystal and the method of applying infrared light used in the micro-spectroscopic measuring device. FIG. 8 is a plan view of the spectroscopic element 200 formed of an array of defect-containing photonic crystals, in which 500 denotes an infrared light source, and 501 denotes a cylindrical lens made of a material with a large refraction index and a high transmissivity for infrared light, such as Si, among materials shown in Table 1. In this embodiment, as shown in FIG. 8, when infrared light emitting from an infrared light source 500 is converted by a cylindrical lens 501 to parallel lights and the infrared light is irradiated from the defect-containing photonic crystals 103 and the side surface of the array 107, the emitted infrared light is emitted from the defect portions 104. In this case, because the infrared light is irradiated from the side wall, the light can travel with less absorption loss by infrared light transmission through the Si host material. The infrared light source 500 and the cylindrical lens 501 can be formed together on the spectroscopic element 200. When the cylindrical lens 501 is formed on the spectroscopic element 200, it is possible to perform operations of the semiconductor manufacturing process, such as etching, together with the spectroscopic element, for example, using the photonic crystal.

Fifth Embodiment

Figure 9:
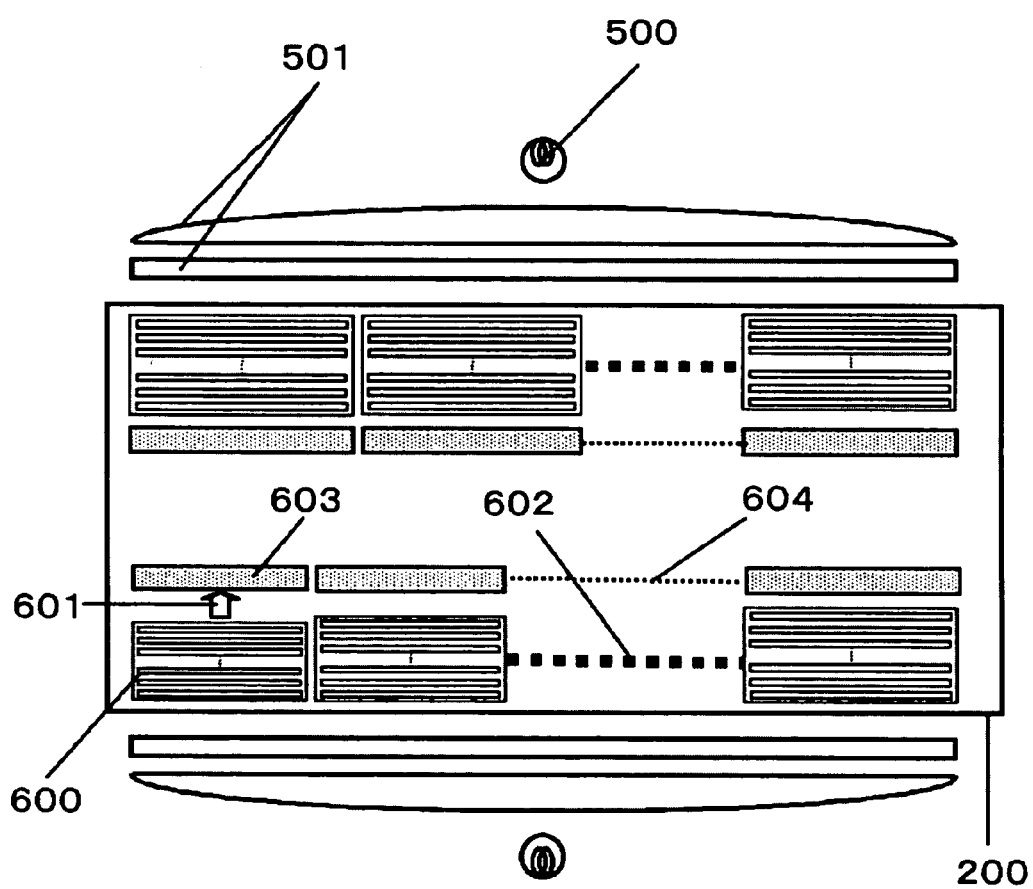
FIG. 9 is a plan view of the spectroscopic element formed by an array of photonic crystals used in the micro-spectroscopic measuring device according to the present invention.

In this embodiment, description will be made of a case where the infrared light source 500 and the cylindrical lens 501 are arranged in the same way as in the fourth embodiment and the photonic crystal is changed from the two-dimensional type to the one-dimensional type. FIG. 9 is a plan view of the spectroscopic element 200 formed of an array of photonic crystals. In FIG. 9, 600 denotes a basic unit of a so-called defect-containing one-dimensional photonic crystal. The one-dimensional photonic crystal is made of a Si layer as the host material, in which a plurality of plate-shaped through-holes are formed and arranged in parallel, and as a defect, the period of the through-holes is partially varied. Those through-holes may be filled with a material, such as barium titanate. Numeral 601 denotes the emitted infrared light emitted from the basic unit of the defect-containing one-dimensional photonic crystal, and 602 denotes an array of basic units 600 of the defect-containing one-dimensional photonic crystal. Those basic units 600 are designed to have the through-holes arranged with different periods, so that they can emit light rays of different wavelengths. Reference numeral 603 denotes a mirror to direct the emitted infrared light 601 to the direction of the flow paths, and 604 denotes an array of the mirrors 603. When one-dimensional photonic crystals are used as in this embodiment, the light injected into the photonic crystal is reflected repeatedly within the crystal, and therefore the light rays of specific wavelengths, which correspond to the periods of the periodic structure of the crystals, are emitted. If defects are introduced in the periodic structure, the intensity of the harmonic components of the specific wavelength to the specific wavelength above mentioned among the emitted light rays can be suppressed, and the monochromaticity of the emitted light rays can be improved. In this embodiment, by the defect-containing photonic crystal 600, the emitted infrared light 601 is emitted into the flat surface of the spectroscopic element 200, and by providing mirrors coated with a metal such as aluminum at an angle of 45 degrees to the emitted infrared light, for example, the emitted infrared light 601 can be reflected in a vertical direction and made to radiate the flow path located right above the photonic crystals. The infrared light source 500 and the cylindrical lens 501 can be formed together on the spectroscopic element 200. Instead of arranging each of the mirrors 603 for each of the basic units 600 of the one-dimensional photonic crystal such as the array 604, a mirror which is long enough to reflect the emitted light from a plurality of the basic units 600 of one-dimensional photonic crystals may be used.

Sixth Embodiment

Figure 10:
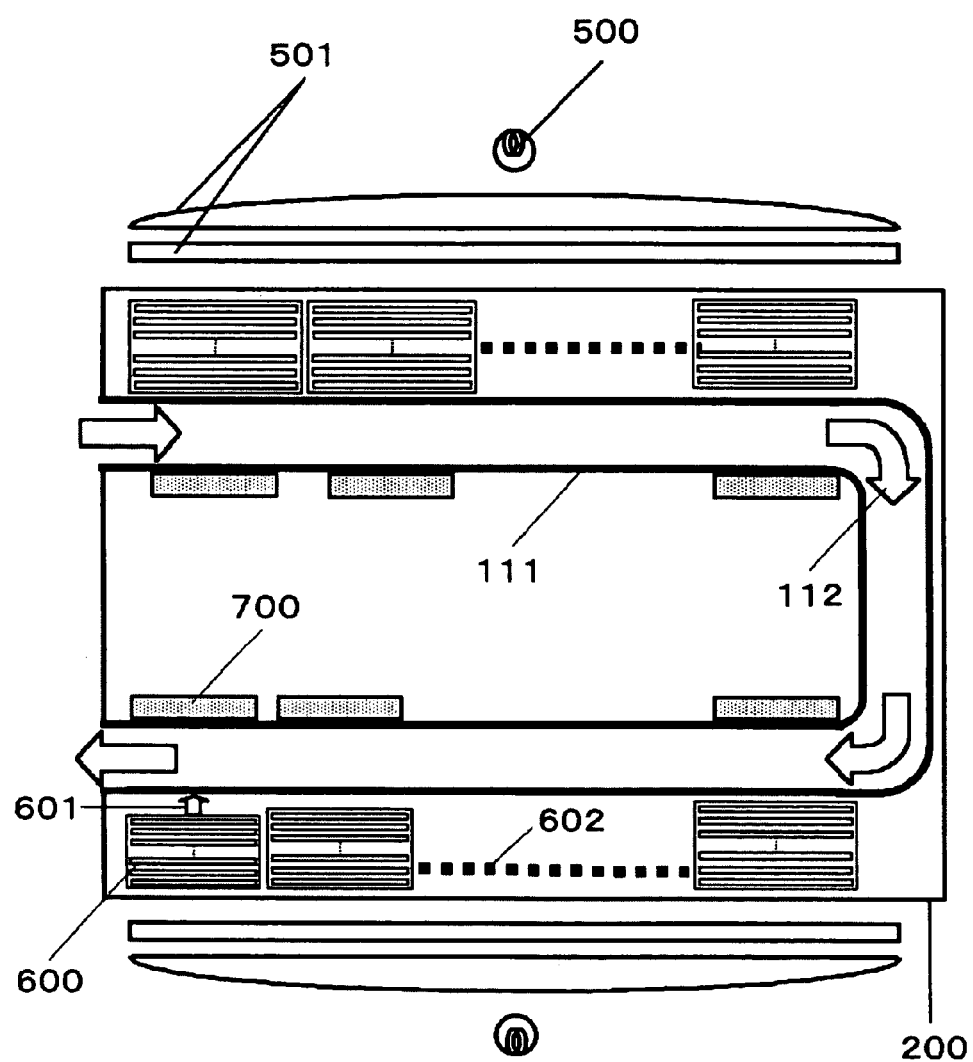
FIG. 10 is a plan view of the spectroscopic element formed by an array of photonic crystals used in the micro-spectroscopic measuring device according to the present invention.

In this embodiment, description will be made of a case where as in the fifth embodiment, the infrared light source 500 and the cylindrical lens 501 are arranged in the same manner as in the fourth embodiment, the photonic crystals are changed from the two-dimensional type to the one-dimensional type, and some changes are made to the layout of the micro flow path 111 for sample. FIG. 10 is a plan view of the spectroscopic element 200, which is formed of an array of photonic crystals including the micro flow path 111 for sample. Reference numeral 700 denotes a light detecting element with a sensitivity to wavelengths from a near-infrared to infrared bandwidth. In this embodiment, by the defect-containing one-dimensional photonic crystals 600, the emitted infrared light 601 is emitted in the plane of the spectroscopic element 200, and the absorption of the emitted infrared light 601 by the sample flow 112 is measured by the light detecting elements 700 through the micro flow path 111 for sample. Consequently, without using the mirrors 603 as shown in the fifth embodiment, it becomes possible to measure the absorption spectrum of the emitted infrared light 601. Further, both the infrared light source 500 and the cylindrical lens 501 can be formed together on the spectroscopic element 200.

Seventh Embodiment

Figure 11:
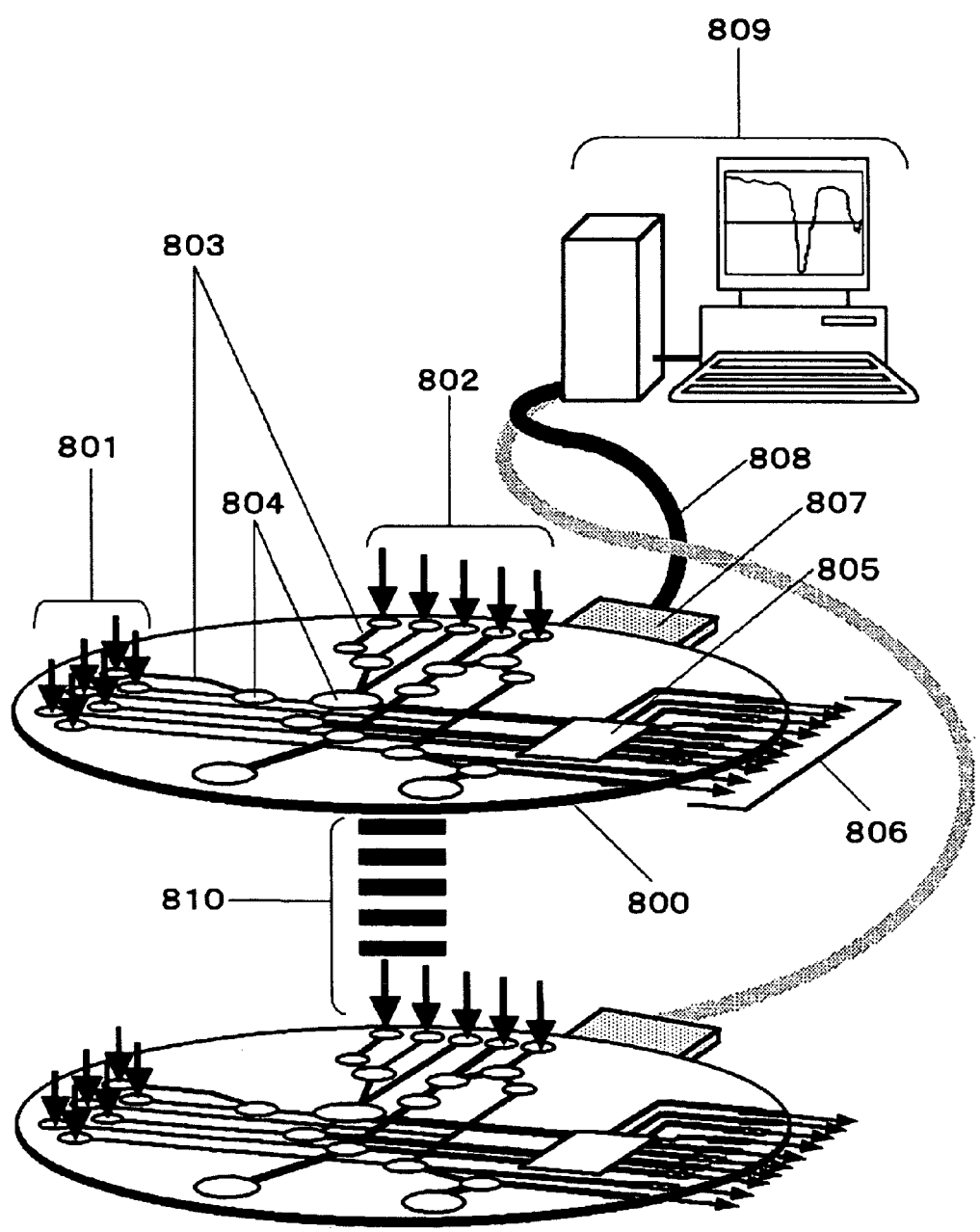
FIG. 11 is a plan view of the spectroscopic element formed by an array of photonic crystals used in the micro-spectroscopic measuring device according to the present invention.

In this embodiment, description will be made of a case where unlike the separate provision of the micro-chemical plant and the micro-spectroscopic measuring device in the second embodiment, the micro-chemical plant and the micro-spectroscopic measuring device are integrated on the same wafer. In FIG. 11, 800 denotes a wafer; 801, 802 denote raw materials; 803 denotes micro flow paths for sample, to which micro pumps and micro valves are included; 804 denotes a micro reactors; 805 denotes a unit of micro-spectroscopic measuring device; 806 denotes synthetic substances; 807 denotes a connector; 808 denotes a cable; 809 denotes a computer for control; and 810 denotes a stack of wafers 800. In this embodiment, materials 801, 802 are supplied and made to react with each other by micro reactors 804 through the micro flow paths for sample 803, their infrared absorption spectra are measured by the micro-spectroscopic measuring device 805, and synthesized substances are identified and extracted from the wafer 800 as synthetic substances 806. Therefore, synthesis and identification of chemical substances can be done on a single wafer 800. A series of synthesis operations and a compounds measuring operation can be controlled sequentially by a computer 809 through the connector 807 and the cable 808. By stacking up a plurality of wafers 800 to thereby form a multi-plate stack 810 of wafers 800, the yield of synthetic substances per unit volume can be increased. For this reason, space saving of the chemical plant and a whole chemical system can be realized.

As has been described, according to the present invention, it is provided a micro-spectroscopic measuring device which has integrated on a chip of not more than several square centimeters functions capable of molecule identification or product quantity measurement by measuring absorption spectra of reaction products.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. The micro-spectroscopic measuring device comprising:
   a spectroscopic element having a light introducing part and a light emitting part;
   a light detecting element; and
   a sample flow path formed between said light emitting part and said light detecting element; and
   a waveguide of light formed on said substrate,
   wherein said spectroscopic element, said light detecting element, and said sample flow path are formed on a substrate
   wherein said waveguide of light and said spectroscopic element are arranged side by side,
   wherein said spectroscopic element is formed from a photonic crystal with defects, and
   wherein said photonic crystal has a periodic structure that a first material and a second material having a lower index of refraction than said first material are periodically repeated and arranged.

2. The micro-spectroscopic measuring device according to claim 1, wherein said spectroscopic element is formed from a plurality of photonic crystals, and wherein said plurality of photonic crystals produce emitted rays of different wavelengths with respect to an incident light ray.

3. The micro-spectroscopic measuring device according to claim 2, wherein each period of said periodic structure of said plurality of photonic crystals is different.

4. The micro-spectroscopic measuring device according to claim 1, wherein said photonic crystal is a two-dimensional photonic crystal.

5. The micro-spectroscopic measuring device according to claim 4, wherein said two-dimensional photonic crystal has a structure that a plurality of columnar pieces of said second material are arranged periodically in said first material or a structure that a plurality of columnar pieces of said first material are arranged periodically in said second material.

6. The micro-spectroscopic measuring device according to claim 1, wherein said photonic crystal is a one-dimensional photonic crystal.

7. The micro-spectroscopic measuring device according to claim 6, wherein said one-dimensional photonic crystal has a structure that a plurality of plate-shaped pieces of said second material are arranged mutually in parallel and periodically in said first material or a structure that a plurality of plate-shaped pieces of said first material are arranged mutually in parallel and periodically in said second material.

8. The micro-spectroscopic measuring device according to claim 1, wherein said first material or said second material is vacuum or air.

9. The micro-spectroscopic measuring device according to claim 1, wherein said spectroscopic element includes a host material layer made of said first or second material and a clad layer adjacent to said host material layer.

10. The micro-spectroscopic measuring device according to claim 9, wherein said first or second material is silicon, and wherein said clad layer includes at least one of air, vacuum and silicon oxide.

11. The micro-spectroscopic measuring device according to claim 1, wherein a wavelength of light emitted from said spectroscopic element is in a band from near infrared to infrared, wherein said light detecting element has a sensitivity to light in a band from near infrared to infrared, and wherein as the flow path of sample, there is provided a tube made of material which transmits light in a band from near infrared to infrared.

12. The micro-spectroscopic measuring device according to claim 11, wherein the material of said tube includes at least one of silicon, calcium fluoride and lithium fluoride.

13. The micro-spectroscopic measuring device according to claim 11, wherein response characteristic of said light detecting element to light in a band from near infrared to infrared is a linear response.

14. The micro-spectroscopic measuring device according to claim 1, wherein as the flow path of sample, a tube is provided, and wherein at least one of said spectroscopic element, said tube and said light detecting element has an alignment mark or a jig for alignment.

15. A micro-chemical system having a micro-spectroscopic measuring device for conducting spectral analysis of a sample introduced, means for introducing a sample to said micro-spectroscopic measuring device, and a light source for emitting light incident on said micro-spectroscopic measuring device, said micro-chemical system comprising:
   a substrate;
   a spectroscopic element having a light introducing part and a light emitting part;
   a light detecting element; and
   a flow path of sample formed between said light emitting part and said light detecting element,
   wherein said spectroscopic element, said light detecting element and said flow path of sample are formed on said substrate of said micro-spectroscopic measuring device,
   wherein said waveguide of light and said spectroscopic element are arranged side by side, and
   wherein there is provided another substrate having said means for introducing sample, said another substrate being different from that of said micro-spectroscopic measuring device, wherein said another substrate is provided with a function to perform at least one of mixing, reaction and separation to said sample, and wherein said micro-spectroscopic measuring device is provided with a connection part to guide the sample from said another substrate to said flow path of sample.

16. The micro-chemical system according to claim 15, wherein said micro-spectroscopic measuring device, said means for introducing a sample and said light source are formed on the same substrate.

* * * * *